United States Patent [19]
Yoder et al.

[11] Patent Number: 6,135,719
[45] Date of Patent: Oct. 24, 2000

[54] METHOD AND APPARATUS FOR METERING INJECTION PUMP FLOW

[75] Inventors: Perry D. Yoder; Kenneth W. Hine, both of Lake Charles, La.

[73] Assignee: OilQuip, Inc., Lake Charles, La.

[21] Appl. No.: 08/999,213

[22] Filed: Dec. 29, 1997

[51] Int. Cl.$^7$ .................................................. B67D 5/08
[52] U.S. Cl. ............................ 417/43; 137/99; 137/551
[58] Field of Search .................... 137/99, 551; 222/63; 417/2, 43, 53, 225, 342, 397, 415, 401

[56] References Cited

U.S. PATENT DOCUMENTS

| | | | |
|---|---|---|---|
| 4,008,829 | 2/1977 | Chandra et al. | 222/63 |
| 4,119,113 | 10/1978 | Meginniss, III | 137/99 |
| 4,370,996 | 2/1983 | Williams | 137/99 |
| 4,389,163 | 6/1983 | Magnussen, Jr. et al. | 417/2 |
| 4,452,573 | 6/1984 | Samuel | 417/401 |
| 4,509,903 | 4/1985 | Fram | 417/464 |
| 4,547,134 | 10/1985 | Hirvonen | 417/349 |
| 4,568,248 | 2/1986 | Harders | 417/43 |
| 4,661,321 | 4/1987 | Byrd et al. | 422/111 |
| 4,701,112 | 10/1987 | Eisenhut et al. | 417/345 |
| 4,795,314 | 1/1989 | Prybella et al. | 417/43 |
| 4,858,645 | 8/1989 | Reeves | 137/551 |
| 4,883,409 | 11/1989 | Strohmeier et al. | 417/43 |
| 5,088,902 | 2/1992 | Marioni | 417/415 |
| 5,092,744 | 3/1992 | Boers et al. | 417/397 |
| 5,209,649 | 5/1993 | Dose et al. | 417/342 |
| 5,755,559 | 5/1998 | Allington et al. | 417/53 |
| 5,879,137 | 3/1999 | Yie | 417/225 |

*Primary Examiner*—Teresa Walberg
*Assistant Examiner*—Leonid Fastovsky
*Attorney, Agent, or Firm*—Fletcher, Yoder & Van Someren

[57] ABSTRACT

A system for metering a fluid, such as a catalyst in an industrial chemical process plant, includes a controller, a drive pump assembly and an injection pump assembly. The drive pump assembly forces reciprocation of the injection pump assembly via a controlled flow of hydraulic fluid. The injection pump assembly includes a drive cylinder and at least one injection section. The drive cylinder receives pressurized fluid from the drive pump assembly and causes metered fluid to be drawn into and expelled by the injection section. The position of reciprocating components of the injection pump assembly is detected between stroke limits and converted to a velocity signal. Closed-loop control of the flow from the injection pump assembly is implemented by the controller via the drive pump assembly based upon the actual velocity of the reciprocating components of the injection pump assembly and a commanded velocity. The closed-loop injection rate control may be incorporated in a nested fashion with a process parameter control loop to maintain a desired level of a process parameter, such as temperature in a reaction vessel.

21 Claims, 5 Drawing Sheets

METHOD AND APPARATUS FOR METERING INJECTION PUMP FLOW

BACKGROUND OF THE INVENTION

1. Field of the Invention

The present invention relates generally to the field of injection pumps and metering devices, particularly for high pressure fluids, such as chemicals and catalysts. More particularly, the invention relates to a technique for metering the flow from a reciprocating injection pump at precise rates based upon closed-loop control of a parameter closely related to actual flow from the injection pump.

2. Description of the Related Art

Many industrial processes require the injection of fluids at very precise rates. For example, in the manufacture of synthetic plastics and other chemical products, high pressure catalysts are injected into process streams to facilitate or accelerate chemical reactions. Because the chemical compositions of the catalysts are often critical to the promotion of the large scale chemical reactions occurring in such processes, their carefully controlled injection into the process stream is often key to obtaining consistent, high quality product. In typical industrial chemical processes catalysts must be injected at precise volumetric or mass flow rates into relatively much larger flows of raw and intermediate products. In addition to promoting the desired chemical reactions, the catalysts often affect important process parameters such as pressure and temperature in process machinery and reaction vessels.

Various apparatus have been proposed and are currently in use for injecting catalysts into chemical process streams. Because many industrial chemical reactions occur at elevated pressures, such structures have been adapted to inject catalyst at very high pressures and precise flow rates. In one known arrangement, a reciprocating plunger-type injection pump is driven by a hydraulic drive cylinder disposed coaxially with the injection pump. The drive cylinder retracts to draw catalyst into the injection pump and extends to express catalyst, via appropriate high pressure valving, into the process stream or reaction vessel. Flow from a hydraulic pump coupled to the drive cylinder is controlled to meter the flow from the injection pump. The hydraulic drive cylinder may be provided with a rod on either side of its piston, permitting it to drive two plunger-type injection pumps on either end of the cylinder. In the latter case, output from the injection pumps is typically combined, via a shuttle valve or similar arrangement, to provide a near steady flow of catalyst as the hydraulic drive cylinder and associated injection pumps continuously reciprocate under the influence of pressurized fluid from the hydraulic pump. Proximity sensors or similar limit switch devices may be associated with the hydraulic drive cylinder or the injection pumps to automatically shift directional control valving between the hydraulic pump and the drive cylinder, causing the drive cylinder and injection pumps to automatically reciprocate between stroke limits.

While control of such systems may be closed-loop with respect to output flow from the hydraulic drive pump, control of the output flow rate of the injection pump itself is typically open-loop. For example, in one known catalyst injection system a drive cylinder is powered by a swash plate-type variable-volume, axial-piston drive pump. The output flow rate of the drive pump may be varied by movement of a swash plate against which a rotating piston set rides. Control circuitry associated with the pump generates a position command for the swash plate based on a desired level of a process parameter, such as temperature. A sensor positioned in the reaction vessel or process stream plumbing provides a feedback signal indicative of the actual level of the process parameter. The swash plate position command is generated by the control circuitry based upon known relationships between the process parameter and catalyst injection rate, the drive pump output flow rate and the swash plate position, and the drive pump output flow rate and the capacity of the drive cylinder (i.e. the effective cross-sectional area of the drive cylinder). The control circuitry regulates the swash plate position in a closed-loop manner, but only so as to maintain the swash plate in the commanded positions. No control loop is closed on the actual output flow from the injection pump, or any parameter directly indicative of the injection rate.

In another known arrangement, a metering valve is provided between the drive pump and the drive cylinder. The metering valve is modulated to control flow into the drive cylinder based upon the desired and actual levels of a process parameter, such as reaction temperature. However, as in the previous case, no control loop is closed on actual injection rate or any parameter closely associated with the actual rate.

Such systems are often incapable of providing sufficiently precise control of high pressure catalyst injection. For example, in the manufacture of polyethylene, reaction vessel pressures in excess of 1,000 bar are not uncommon. Depending upon the throughput of the reaction vessel, precise catalyst injection rates on the order of only several cubic centimeters per minute may be demanded of the catalyst injection pump system. However, very slight variations in the catalyst injection rate may result in dramatic swings in process temperature and pressure. It has been found that catalyst injection systems of the types described above can produce variations in catalyst injection rates from desired levels in excess of tolerable ranges as dictated by equipment operating limits and product quality specifications. Such variations may result from factors such as hysteresis in the reciprocating pump velocities, tolerances in drive pump output flow rate, tolerances in metering valve flow, lack of sufficient repeatability in pump or valve set points and corresponding flow rate, and so forth.

Swings in process conditions resulting from such catalyst injection rate variations can not only lead to the production of poor quality or down-graded product, but can necessitate interruption of the plant process and decompression of reaction vessels in other process stream equipment. In the latter case, significant costs can be incurred from down time to purge the process equipment and bring the process back on line, as well as from repair or replacement of damaged equipment. Moreover, even when variations in catalyst flow rate remain within acceptable limits, improved product could often be obtained if process parameters affected by catalyst injection rates, such as reaction temperature, could be more accurately controlled.

There is a need, therefore, for an improved pumping and metering system, particularly for injecting chemicals and catalysts of the type used in industrial chemical processing applications. More particularly, there is a need for an improved metering or injection system capable of providing closed-loop control of actual flow rate, or of a parameter closely indicative of flow rate, from a reciprocating injection pump. Ideally, the technique should be capable of being employed in systems closing a nested control loop on a process variable or parameter, such as reaction pressure or temperature. The technique should also be capable of implementation on new chemical injection systems, as well as afford the possibility of being retrofitted to the many injection systems currently in use.

SUMMARY OF THE INVENTION

The present invention provides a novel injection pump control system designed to respond to these needs. The system is based on a reciprocating hydraulic drive cylinder arrangement coupled with a high pressure plunger-type injection pump. The system may be adapted to control opposed reciprocating plunger-type injection pumps plumbed to provide near continuous injection flow as the hydraulic drive cylinder is stroked. The system closes a control loop on a parameter of the reciprocating drive and injection pumps which is very closely associated with injection pump flow rate. The resulting system is particularly well suited to injection of high pressure fluids, such as catalysts, at very precise rates.

In a preferred embodiment, the displacement velocity of the reciprocating portion of the drive and injection pumps is used as a control variable. The velocity-based control loop serves to command output of a proportional fluid control valve, such as an electrohydraulic servo valve. Alternatively, a variable volume drive pump may be used, and the velocity-based control loop implemented to provide feedback control of the pump output flow rate to maintain the desired velocity and thereby the desired injection rate. The velocity may be measured in a variety of manners, such as by means of a linear position sensor. Because the area of the injection pump plunger is known and fixed, the velocity provides a very reliable indicator of output flow from the injection pump.

Where the system is employed to control injection of catalyst into a process stream, catalyst injection flow command signals may be generated from a measured process parameter, such as temperature. In a preferred embodiment, nested control loops are implemented, a first closed on the process parameter, and a second closed on injection pump flow rate or the parameter closely associated with injection pump flow rate. The resulting system provides very reliable, closed-loop control of catalyst injection, despite tolerances and variations in output hydraulic drive pumps or hysteresis in the reciprocating catalyst injection pumping arrangement.

Thus, in accordance with a first aspect of the invention, an injection pump system is provided which includes a pump body, a reciprocating assembly, a drive pump unit, a sensor assembly, and a control circuit. The pump body includes a metering section and drive section coaxially coupled to the metering section. The reciprocating assembly includes a plunger disposed in the metering section, a piston disposed in the drive section, and a rod drivingly coupled to the piston and the plunger. The drive pump unit is coupled to the drive section for supplying pressurized fluid for forcing reciprocation of the reciprocating assembly with respect to the pump body between predetermined stroke limits. The sensor assembly is configured to generate a parameter signal representative of position of the reciprocating assembly with respect to the pump body between the stroke limits. The control circuit is coupled to the drive pump unit and to the sensor assembly. The control circuit is configured to generate a velocity signal from the parameter signal, to compare the velocity signal to a velocity command signal, and to regulate flow of pressurized fluids from the drive pump unit to the drive section based upon the velocity signal and the velocity command signal.

In accordance with another aspect of the invention, an injection pump drive system is provided for controlling a reciprocating injection pump. The injection pump is of the type including a pump body having a metering section and a drive section coaxially coupled with another, and a reciprocating assembly including a plunger disposed in the metering section, a piston disposed in the drive section, and a rod drivingly coupled to the piston and to the plunger. The reciprocating assembly is movable with respect to the pump body between predetermined stroke limits. The drive systems includes the drive pump unit, a sensor assembly, and a control circuit. The drive pump unit is coupled to the drive section for forcing reciprocation of the reciprocating assembly. The sensor assembly is configured to generate an input signal indicative of actual flow rate from the injection pump during movement of the reciprocating assembly between the stroke limits. The control circuit is coupled to the sensor assembly and to the drive pump unit. The control circuit is configured to compare the input signal to a command signal indicative of a desired flow rate from the injection pump. The control circuit generates control signals based upon the input and command signals, and applies the control signals to the drive pump unit to regulate flow of pressurized fluid from the drive pump unit, and thereby to control the flow rate from the injection pump.

The invention also provides a method for metering pressurized flow from a reciprocating injection pump. The injection pump includes a pump body having a metering section and a drive section coaxially coupled to the metering section. A reciprocating assembly comprises a plunger disposed in the metering section and a piston disposed in the drive section, along with a rod drivingly coupled to the piston and the plunger. A drive pump unit is coupled to the drive section for supplying a flow of pressurized fluid for forcing reciprocation of the reciprocating assembly with respect to the pump body between predetermined stroke limits at desired velocities. The method includes a first step of generating a velocity command signal representative of a desired velocity of the reciprocating assembly with respect to the pump body. An actual velocity signal is then generated representative of the actual velocity of the reciprocating assembly with respect to the pump body. The velocity command signal and the actual velocity signal are compared and a drive command signal is generated based thereon. The flow of pressurized fluid from a drive pump unit to the drive section is then regulated based upon the drive command signal.

In accordance with a further aspect of the invention, a method is provided for controlling the rate of chemical injection into a process stream by a reciprocating injection pump. The injection pump includes a pump body having a metering section and a drive section coaxially coupled to one another. A reciprocating assembly includes a plunger disposed in the metering section, a piston disposed in the drive section, and a rod drivingly coupled between the piston and the plunger. A drive pump unit is coupled to the drive section for supplying a flow of pressurized fluid for forcing reciprocation of the reciprocating assembly with respect to the pump body between predetermined stroke limits at desired velocities. The method includes a first step of sensing a parameter of the process stream and generating a parameter signal representative thereof. An injection rate command signal is then derived from the parameter signal. The injection rate command signal is converted to an injection pump velocity command signal. The reciprocating assembly is then driven at a predetermined velocity with respect to the pump body based upon the velocity command signal. An actual velocity signal is generated which is representative of the velocity of the reciprocating assembly with respect to the pump body. The actual velocity signal is compared to the velocity command signal, and the velocity of the reciprocating assembly is regulated to maintain a desired level. In a particularly preferred embodiment of the method, signals are generated that are indicative of positions of the reciprocating assembly between the stroke limits are detected and the actual velocity signal is derived from the position signals.

BRIEF DESCRIPTION OF THE DRAWINGS

The foregoing and other features and advantages of the invention will become apparent upon reading the following detailed description and upon reference to the drawings in which.

DETAILED DESCRIPTION OF SPECIFIC EMBODIMENTS

Figure 1:
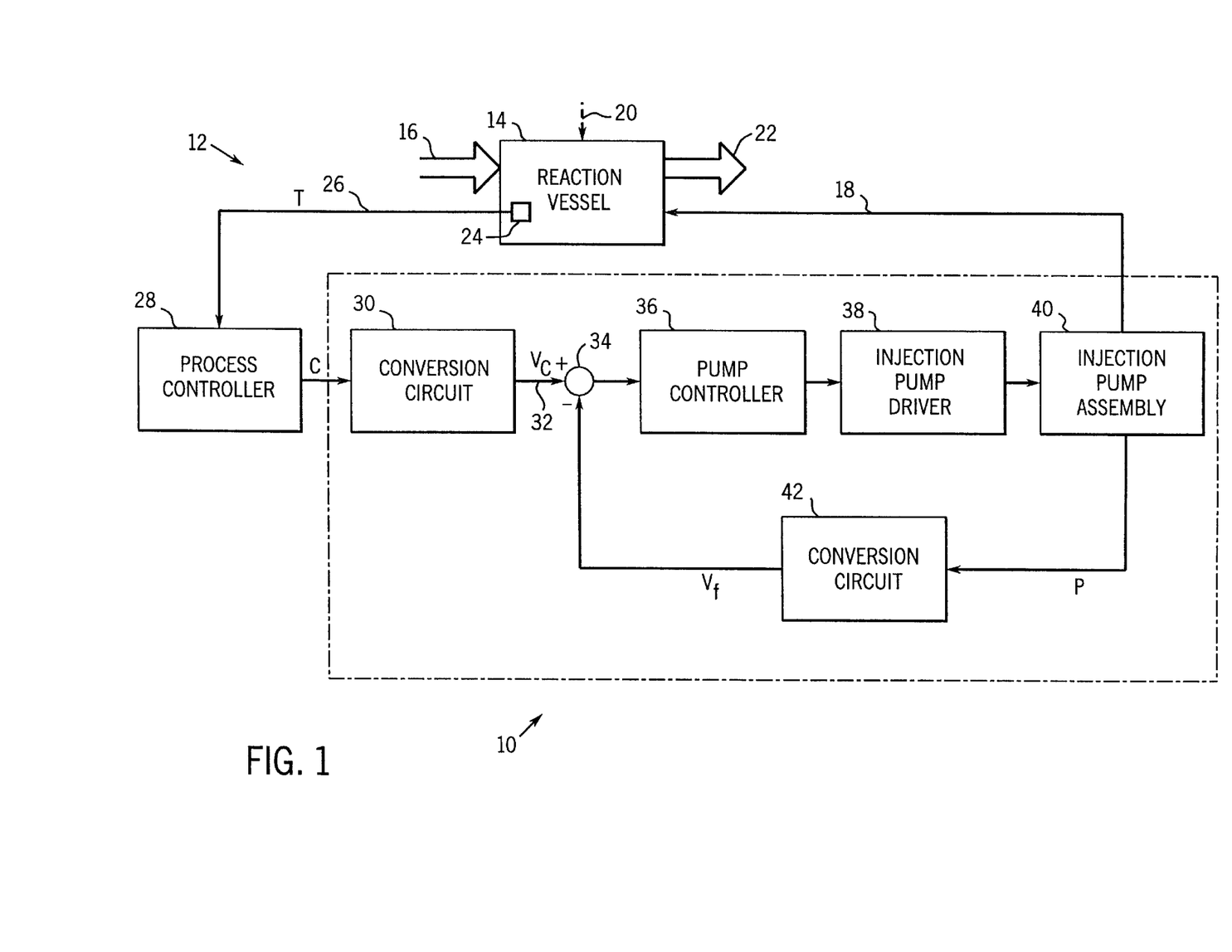
FIG. 1 is a diagrammatical representation of a chemical reaction plant coupled to a catalyst injection and control system in accordance with certain aspects of the invention.

Turning now to the drawings, and referring first to FIG. 1, an injection or metering system, designated generally by reference numeral 10 is illustrated coupled to a process plant 12. As will be appreciated by those skilled in the art, process plant 12 may comprise a variety of industrial chemical process equipment, including pumps, valves, transfer conduits, and so forth for combining or refining specific chemical substances to produce a desired intermediate or final product. In particular, process plant 12 may include polymerization equipment used to produce polymer chains, such as polyethylene, polypropylene and so forth. Plant 12 includes a reaction vessel 14 which receives a process stream 16 of substances to be combined or refined therein. Vessel 14 also receives a flow of metered catalyst 18 used to facilitate or promote the desired reaction within vessel 14. As will be also be appreciated by those skilled in the art, the particular catalyst utilized within vessel 14 and the mass flow rate of catalyst will depend upon the type of process on which system 10 is installed, the mass flow rate of the process stream 16, process parameters such as temperature or pressure to be maintained in vessel 14, and so forth. Moreover, reaction vessel 14 may receive flows of additional products 20. Following the desired reaction or refining operation taking place in reaction vessel 14, an outflow 22 is produced which is transferred to downstream processing equipment (not represented) for further refining or processing.

Reaction vessel 14 (or process equipment and conduits associated with reaction vessel 14) is preferably instrumented with various sensors for detecting key process parameters, such as pressure, temperature and so forth. As illustrated in the diagrammatical representation of FIG. 1, a sensor 24 is associated with reaction vessel 14 for detecting one such parameter, namely temperature. Sensor 24 may be of any suitable type, such as a thermocouple configured and calibrated to generate electrical signals representative of the temperature within vessel 14. An output signal from the sensor is transmitted along a data link 26 to a process controller 28. Process controller 28 may include a range of industrial control hardware and software, but preferably includes a microprocessor-based industrial computer for controlling various aspects of processing plant 12.

In the particular process illustrated in FIG. 1, process controller 28 receives the temperature signal from sensor 24 and generates command signals for increasing or decreasing the catalyst flow rate to maintain a desired temperature level or band. Alternatively, controller 28 may generate an absolute flow rate command based, for example upon the mass flow rate of process stream 16, and upon known relationships between the process stream and the flow of catalyst 18. As will be appreciated by those skilled in the art, the flow of catalyst into reaction vessel 14 must generally be matched to the flow of the process stream 16 to obtain a steady state production throughput of plant 12, maintain desired levels of process parameters such as temperature and pressure within vessel 14, and produce an outflow 22 of an intermediate or final product having desired physical and chemical attributes. Moreover, while such steady state conditions may be maintained by feedback control of system 10 as described more fully below, those skilled in the art will appreciate that the catalyst flow rate command signal (represented generally by the letter "C") may be altered during various phases of operation of processing plant 12, such as during start-up, shut down, and so forth.

Process controller 28 transmits catalyst flow rate command signal C to injection system 10. As shown in FIG. 1, injection system 10 includes a conversion circuit 30, summer 34, an injection pump controller 36, an injection pump driver 38, an injection pump assembly 40, and a feedback conversion circuit 42. In general, conversion circuit 30, summer 34, pump controller 36 and conversion circuit 42 may be physically defined by circuitry and programming code in a microprocessor-based controller of a type generally known in the art. Because injection system 10 includes a reciprocating pump assembly of known physical geometry, a desired flow rate of catalyst from system 10 can be converted to a desired velocity of a reciprocating assembly by dividing the mass flow rate of catalyst by the cross-sectional area of injection or metering plungers of the injection system. Thus, a velocity command signal $V_c$ is generated by conversion circuit 30 based upon the flow rate command signal C. In a presently preferred embodiment, process controller 28 produces a flow rate command signal C which is a 4 to 20 mA signal, applying the signal to conversion circuit 30. Conversion circuit 30 is calibrated to produce a velocity command signal $V_c$ over a predetermined range scaled to the 4 to 20 mA signal received from process controller 28. The range of velocity command signal $VC_c$, in turn, corresponds to a flow rate range of catalyst from injection system 10, such as zero to 40 gallons per hour. Conversion circuit 30 outputs velocity command signal $V_c$ in a digitized form. As will be appreciated by those skilled in the art, however, the particular scaling implemented by conversion circuit 30 will depend upon the particular controller and software selected. Moreover, velocity command signal $V_c$ output by conversion circuit 30 may be an analog signal. Conversion circuit 30 transmits velocity command signal $V_c$ to summer 34 as indicated at reference numeral 32, as an input command signal for a feedback loop used to meter catalyst to reaction vessel 14 as described below.

In general, summer 34 receives velocity command signal $V_c$ and compares the command signal to a velocity feedback signal $V_f$ from conversion circuit 42. The resulting velocity error signal is applied to pump controller 36. Pump controller 36, which preferably includes an appropriately programmed industrial computer or programmable logic controller, generates drive signals for commanding injection pump driver 38 based upon the velocity command and feedback signals. In a particularly preferred embodiment, pump controller 36 implements a proportional-integral-derivative (PID) control algorithm for maintaining velocity of a reciprocating assembly within injection pump assembly 40 at the desired level $V_c$.

Figure 2:
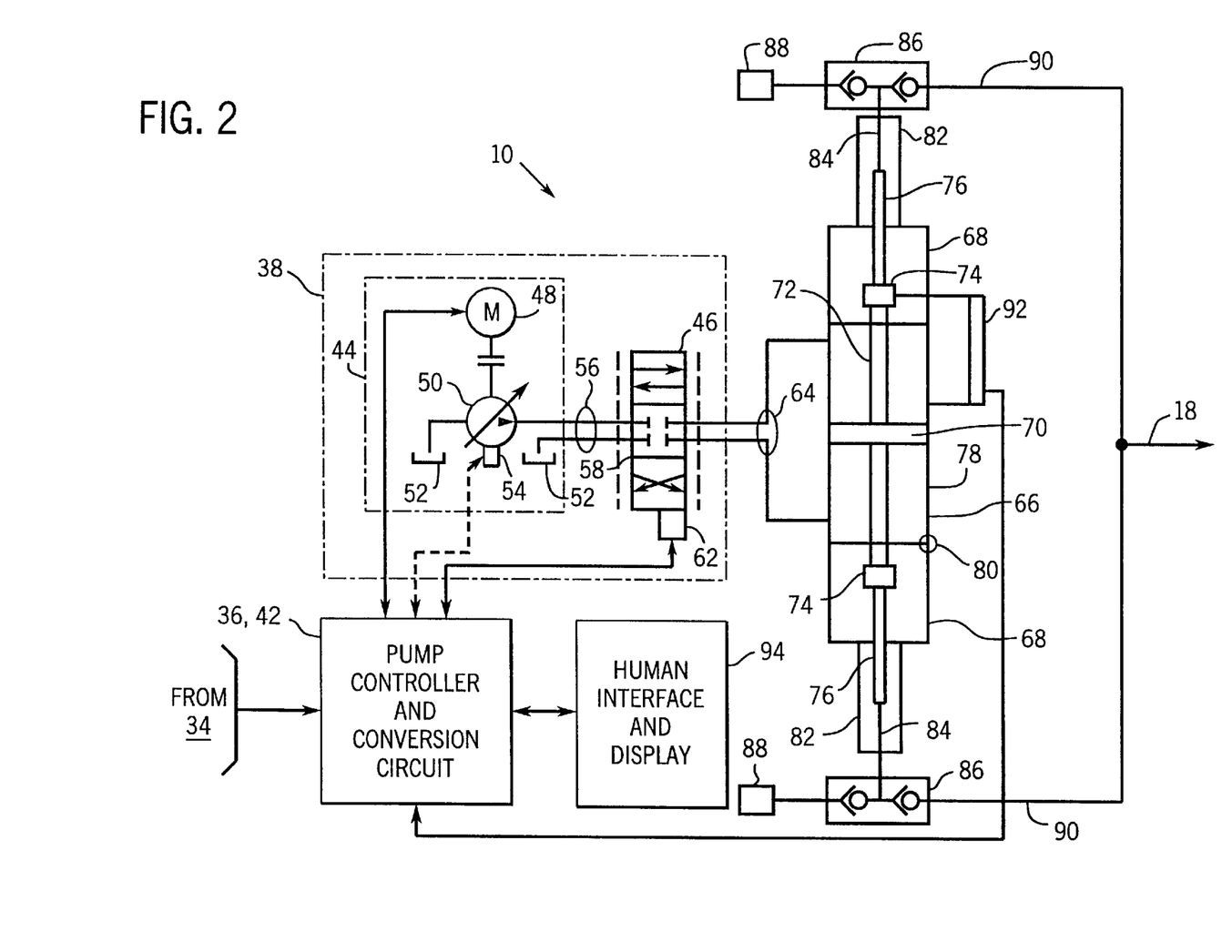
FIG. 2 is a diagrammatical representation of an injection or metering system for use in controlled injection of a catalyst or other substance in an arrangement of the type illustrated in FIG. 1.

FIG. 2 illustrates a particularly preferred configuration of injection system 10, showing additional details of injection pump driver 38 and injection pump assembly 40. As shown in FIG. 2, injection pump driver 38 includes a drive pump assembly 44 coupled to directional control valving 46. Drive pump assembly 44, which is preferably constructed as a stand-alone hydraulic power unit, includes a drive motor 48 coupled to a drive pump 50. While driver motor 48 may be of any suitable type, in the preferred configuration, motor 48 is a polyphase industrial grade alternating current induction motor which is powered and controlled by controller 36. Drive pump 50 is a variable-volume hydraulic piston pump, such as a swash-plate pump configured to provide pressure compensated flow of hydraulic fluid for driving injection pump assembly 40. In operation, motor 48 drives pump 50 to draw hydraulic fluid from a tank or reservoir 52. Pump positioner 54 associated with pump 50 compensates pump 50 to maintain a desired pressure of an output flow from pump 50. As will be appreciated by those skilled in the art, pump positioner 54 orients a control member, such as a swash-plate, so as to maintain the pressure of fluid flowing from pump 50 at or near a desired level despite variations in the flow rate during operation of system 10. As will also be appreciated by those skilled in the art, drive pump assembly 44 may include additional valving, instrumentation and so forth, such as relief valves, pressure gauges, temperature indicators, and so forth.

Drive pump assembly 44 transmits a flow of pressurized hydraulic fluid and receives a return flow of fluid via conduits 56. Conduits 56 extend to input and return ports of valving 46. In the preferred embodiment illustrated, valving 46 includes an electrohydraulic servo valve assembly designed to regulate output flow to injection pump assembly 40 in a manner proportional to an input signal received from pump controller 36. While any suitable type of servo valve may be employed, acceptable valves have been determined to include a type available commercially from Atchley Controls of Salt Lake City, Utah under the commercial designation 211A. Valve 46 is configured to maintain a closed center position 56. A valve positioner 62 shifts valve 46 continuously between supply and return positions in response to control signals from pump controller 36. Controlled flow from valve 46 is then transmitted from injection pump driver 38 to injection pump assembly 40 to control or meter flow therefrom. It should be noted, that although the servo valve illustrated in FIG. 2 is presently preferred, in certain applications, a conventional proportional valve may be employed in place of the servo valve to modulate flow from drive pump assembly 44 to injection pump assembly 40.

Injection pump assembly 40 is preferably a reciprocating pump arrangement which includes a drive cylinder 66 and one or more injection sections 68. Drive cylinder 66 receives pressurized flow from drive pump assembly 44 to force a metered fluid, such as a catalyst, to be drawn into and expressed by injection sections 68. As will be appreciated by those skilled in the art, while a single injection section 68 maybe included in injection pump assembly 40, a pair of injection sections arranged as illustrated in the Figures permits a relatively continuous flow of metered fluid by virtue of common valving downstream of the sections.

In general, drive cylinder 66 includes a peripherally sealed piston positioned along a rod 72. Connectors 74 secure ends of rod 72 to plungers 76 of each injection section 68. Together, piston 70, rod 72, connector 74 and plungers 76 form a reciprocating assembly which oscillates under the influence of pressurized fluid received from valving 46. Drive cylinder 66 further includes a cylinder body 78 in which piston 70 is sealingly received. Interface hardware 80 secures cylinder body 78 to injection section housings 82 on either end thereof A high pressure discharge passage or port 84 is provided through each injection section housing 82 for drawing metered fluid into the housings and for expressing the fluid from the housings. Directional control valving, such as including check valves 86, is coupled to passages 84 to control inflow into and outflow from injection sections 68. Valving 86 is, in turn, coupled to a source 88 of metered fluid, such as catalyst, as well as to a discharge conduit 90. In the illustrated embodiment, discharge conduits 90 from each set of valves 86 are joined to form a common header for the discharge of catalyst, as indicated by reference numeral 18.

In operation, pump controller 36 regulates the flow of pressurized fluid from injection pump driver 38 to maintain a desired flow of fluid from injection pump assembly 40. Thus, pressurized fluid is alternately expressed from valving 46 into sides of cylinder body 78 adjacent to piston 70 to cause reciprocation of the reciprocating elements of injection pump assembly 40. Specifically, because variations in the flow of catalyst 18 may occur due to variations in flow from pump 50, valving 46 is controlled to maintain a desired a velocity of the reciprocating elements of injection pump assembly 40 with respect to stationary elements of the assembly, including cylinder body 78, interface hardware 80, and injection section housings 82 in a closed-loop manner. In heretofore known systems, such variations could result from a number of sources, including changes in discharge load downstream of injection pump assembly 40, hysteresis in valving or drive cylinders, variations in resistance of physical components of the reciprocating assemblies of injection pump assembly 40 and so forth. The closed-loop control implemented by the present technique effectively overcomes errors due to such factors by regulating the actual velocity of reciprocating elements of injection pump assembly 40 as described in greater detail below.

To permit feedback control of the velocity of the reciprocating elements, a feedback sensor assembly 92 is positioned intermediate a reciprocating element and a stationary element of injection pump assembly 40. In the preferred embodiment illustrated, a position sensor is coupled between a connector 74 and interface hardware 80. The sensor generates position signals which are converted to velocity signals as described more fully below. These velocity signals, indicative of the actual velocity of the reciprocating elements of injection pump assembly 40, serve as feedback velocity signal $V_f$ mentioned above with regard to FIG. 1. It should be noted that, as described below, position signals produced by sensor assembly 92 are also used to control automatic reversing of the reciprocating elements of injection pump assembly 40 within predefined stroke limits.

A human interface and display station 94 is preferably associated with pump controller 36 to permit calibration, configuration and diagnostics of injection system 10. In a presently preferred embodiment, human interface and display station 94 includes a programmed personal computer based upon an Intel 486 processor platform.

Figure 3:
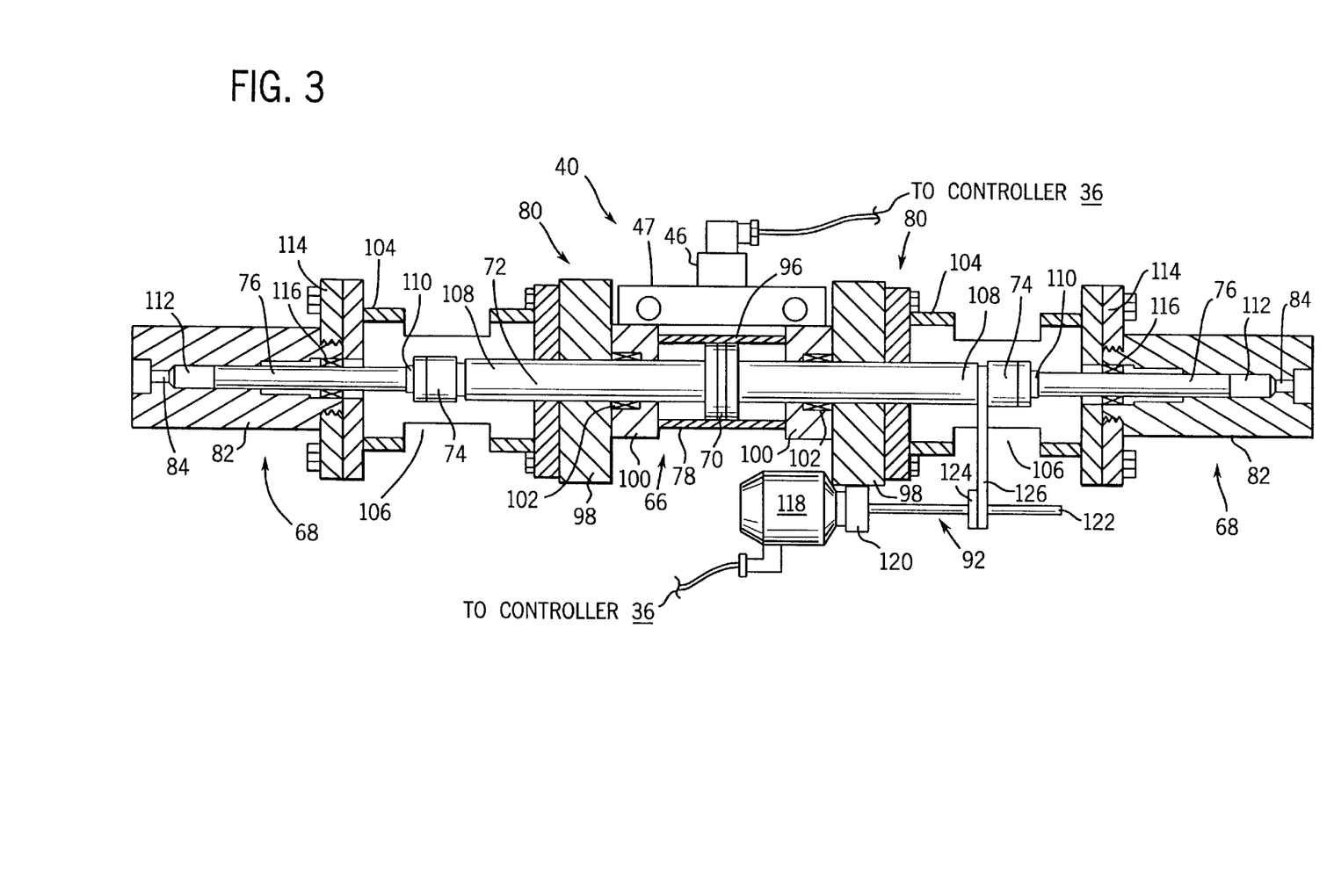
FIG. 3 is a partial sectional representation of an injection or metering system including a drive section and a pair of injection sections.

FIG. 3 illustrates in partial section additional details of a preferred configuration of injection pump assembly 40. As shown in FIG. 3, drive cylinder 66 has a body 78 formed of a shell or barrel 96 in which piston 70 is sealingly positioned. Rod 72 extends from piston 70 through heads 100 which are sealed to barrel 96. High pressure seal assemblies 102 are provided about rod 72 within each head 100. Support blocks 98 are secured to each head 100 and interface with adapter sections 104 to support and space injection sections 68 from drive cylinder 66. Each adapter section 104 includes access ports 106 through which connectors 74 may be installed and subsequently adjusted. In the preferred embodiment illustrated, ends 108 of rod 72 are threaded into connectors 74, which includes lock nut assemblies for maintaining rod 72 in a desired position with respect to plungers 76. Correspondingly, an end 110 of each plunger 76 is secured to connectors 74, such as by a slotted engagement.

Within each injection section 68, plungers 76 are slidingly received within bores 112 formed within the injection section housings 82. As will be appreciated by those skilled in the art, plungers 76 are preferably dimensioned so as to slide within housings 82 to displace fluid, such as catalyst from bores 112. Housings 82 are threadingly secured to heads 114, and high pressure seals 116 are provided between plungers 76 and heads 114. Heads 114 are secured to ends of adapter sections 104 to align shaft 72 and plunger 76 coaxially with one another. As mentioned above, in operation, piston 70, rod 72, connectors 74 and plungers 76 form a reciprocating assembly. Drive cylinder body 78, along with interface hardware 80 (including adapter sections 104) and housings 82, form a stationary structure which is preferably secured on an appropriate machine base (not shown).

Valving 46 and sensor assembly 92 may be conveniently mounted on injection pump assembly 40 as shown in FIG. 3. In the illustrated embodiment, servo valve 46 is mounted on a ported manifold base 47 which is secured to drive cylinder head 100. Output and return flow between valving 46 and drive cylinder 66 may then be conveniently channeled through internal ports between manifold base 47 and drive cylinder head 100.

FIG. 3 also illustrates a presently preferred arrangement of a position sensor assembly for providing feedback signals to pump controller 36. As shown in FIG. 3, sensor assembly 92 is a magnetostrictive position sensor of a type commercially available from MTS Systems Corporation of Cary, N.C. under the commercial designation Temposonics. As will be recognized by those skilled in the art, sensors of this type are capable of providing high precision position feedback signals during movement of the reciprocating components of injection pump assembly 40. Also, where desired, certain of the conversion functions executed by feedback conversion circuit 42 may be provided within sensor assembly 92, providing direct feedback of both velocity and position signals.

In the illustrated embodiment, a sensor body 118 is supported by a support bracket 120 from a support block 98. A sensing wand 122 extends from sensor body 118 through support bracket 120. A magnet 124 is positioned about wand 122 and supported by a magnet support arm 126. Support 126 is, in turn, supported on rod 72 between an end 108 of the rod and a connector 74. In operation, magnet 124 reciprocates with support arm 126 and rod 72. Position signals indicative of the relative position of the reciprocating components of injection pump assembly 40 with respect to the stationary components thereof are thereby generated and transmitted to controller 36 by the sensor assembly.

As will be appreciated by those skilled in the art, a number of alternative configurations for sensing the relative positions of reciprocating and stationary components of injection pump assembly 40 may be envisioned. For example, where a single injection section 68 is employed, a sensor configuration of the type illustrated in FIG. 3 may be used. Alternatively in such cases, a sensor of the type illustrated in FIG. 3 may be positioned such that wand 122 extends through a bore formed in rod 72 on an opposite side of drive cylinder 66 from the single injection section. Moreover, sensors employing technologies other than magnetostrictive techniques may be employed, such as linear encoders, linear potentiometers, inductive sensors and the like. However, because the system described herein provides closed-loop control of injection pump output flow based upon a parameter closely associated therewith, such as velocity of the reciprocating components of assembly 40, the sensing technology employed preferably permits a number of feedback signals to be generated and applied to controller 36 during each reciprocating cycle of pump assembly 40.

Figure 4:
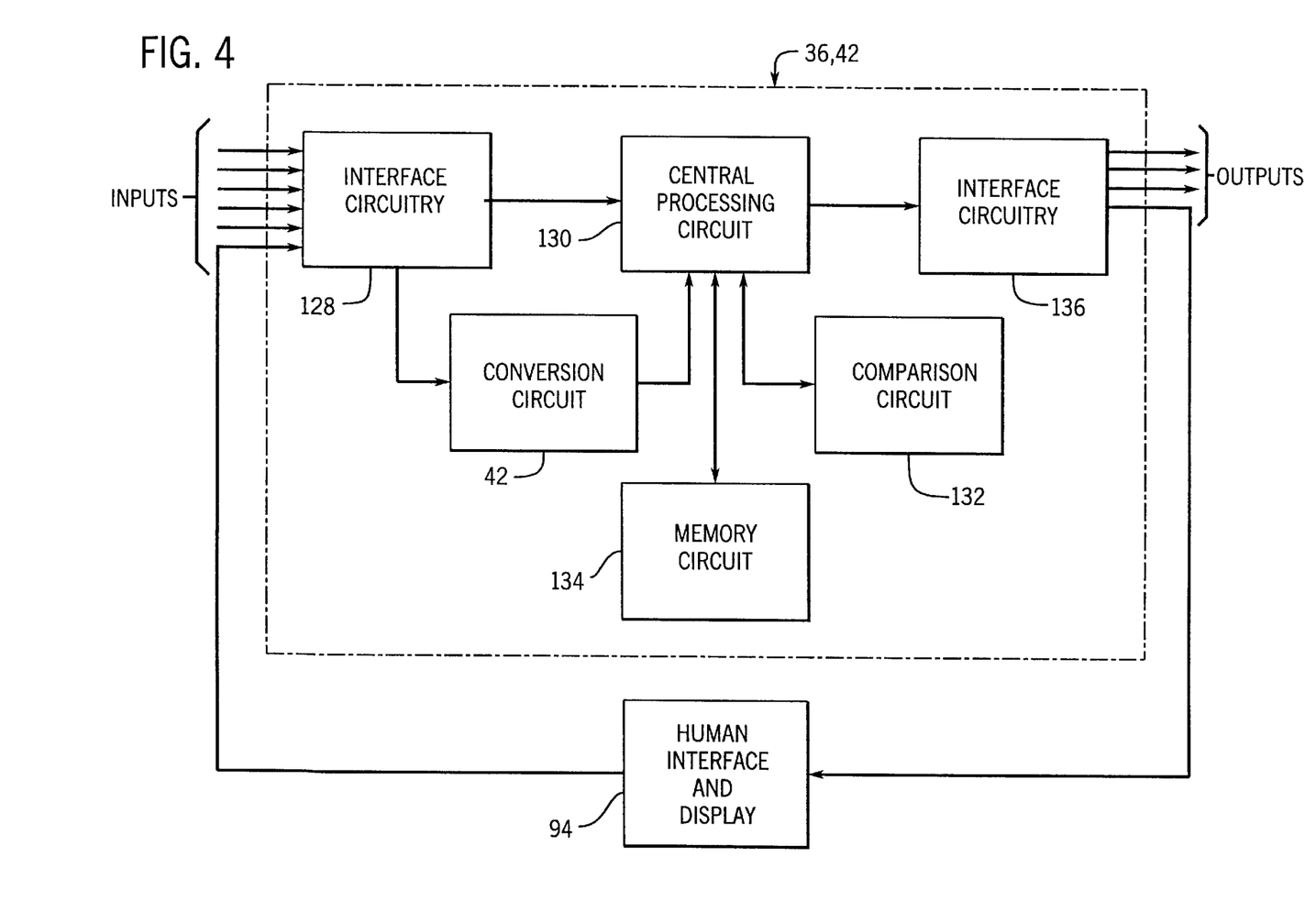
FIG. 4 is a signal flow diagram illustrating certain of the functional circuitry included in a preferred embodiment of a controller for the injection system of FIG. 2.

FIG. 4 illustrates certain of the functional circuitry included in controller 36 in accordance with a presently preferred embodiment of the system. Specifically, controller 36 includes input interface circuitry 128, a central processing circuit 130, a comparison circuit 132, a memory circuit 134, and output interface circuitry 136. Input interface circuitry 128 preferably includes signal conditioning circuitry, such as network interfaces, analog-to-digital converters, multiplexing circuits and so forth, for sampling input command and feedback signals and for applying these signals to conversion circuit 42 and central processing circuit 130. In the presently preferred embodiment, interface circuitry 128 receives signals from summer 34 (or process controller 28) and sensor assembly 92 (see FIGS. 1 and 2). Where the feedback signal returning from sensor assembly 92 is a signal indicative of position, this signal is communicated from interface circuitry 128 to conversion circuit 42 where the time differential of the signal is generated to provide a converted signal representative of the actual velocity of the reciprocating components of injection pump assembly 40. This actual velocity feedback signal is then transmitted to central processing circuit 130. In addition, the actual position signals are also transmitted to central processing circuit 130 and are used to trigger automatic reciprocation of the reciprocating components of assembly 40 between predetermined stroke limits. Also as mentioned above, where desired, conversion circuit 42 may be provided within sensor assembly 92, permitting both position and velocity feedback signals to be fed back directly to central processing circuit 130 via interface circuitry 128.

Central processing circuit 130 implements a cyclical control routine stored in memory circuit 134. In the presently preferred embodiment, during steady state operation, central processing circuit 130 cycles through the control routine to compare velocity command signals to velocity feedback signals and to generate control signals for altering the position of valving 46 to maintain the velocity of the reciprocating components of injection pump assembly 40 at the commanded or desired velocity. The comparison of the command and feedback signals are performed in comparison circuit 132 (effectively constituting summer 34 illustrated in FIG. 1). As will be appreciated by those skilled in the art, where a difference is detected between the desired and actual velocities of the reciprocating components of assembly 40, central processing circuit 130 generates control signals for increasing or decreasing the actual velocity to match the command velocity. These control signals are then communicated to output interface circuitry 136 where they are converted to the appropriate signal types and levels required by valve positioner 62. Such velocity corrections preferably follow a PD controlled algorithm whereby changes in commanded velocities are tracked rapidly by a differential component of the output command signal, while steady state errors are reduced by an integral component of the command signal, as will be appreciated by those skilled in the art. In addition to controlling velocity of the reciprocating components, central processing circuit 130 cyclically compares the actual position fed back from sensor assembly 92 to predetermined stroke limit values, and shifts valving 46 to reverse the direction of movement of the reciprocating components.

Central processing circuit 130 preferably outputs control or command signals to motor 48 via output interface circuitry 136. In the illustrated embodiment, motor 48 is either energized or de-energized, such that interface circuitry 136 includes appropriate relays in series with power conductors for supplying electrical energy to the motor 48. Finally, central processing circuit 130 is preferably configured to output status and diagnostic information regarding the program stored in memory circuit 134, as well as historical information on the actual and command velocities, reciprocating stroke limits, and so forth through output interface circuitry 136 to human interface and display station 94. Station 94 is, in turn, configured to input settings, program alterations, and the like into controller 36 via interface circuitry 128.

Injection system 10 thus provides closed-loop control of the velocity of reciprocating components of assembly 40 and, thereby, of the output flow from injection pump assembly 40. Because the dimensions of bores 112 and plungers 76 are known and fixed, the velocity of reciprocation of plungers 76 is directly proportional to the output flow rate of metered fluid from each injection section 68. Moreover, unlike heretofore known catalyst injection systems, because system 10 closes a control loop on the actual displacement velocity of the reciprocating components, rather than on the position of flow control elements within pump 50 for example, actual injection flow rate may be controlled precisely.

It should also be noted that the control approach implemented by system 10 effectively creates a nested pair of control loops. Specifically, as illustrated in FIG. 1, a first control loop includes reaction vessel 14, process controller 28, system 10, and catalyst flow 18. A process parameter, such as temperature, is used as the basis for closed-loop control in this first loop. A command or desired value of the process parameter is stored in process controller 28, and is maintained by supplying a desired or commanded amount of catalyst flow 18 into reaction vessel 14. Within this control loop, system 10 implements a sub-loop wherein catalyst injection rate is maintained at a desired level as dictated by process controller 28.

While the foregoing embodiment is presently preferred, it should be noted that certain alternative configurations may be envisioned by those skilled in the art for regulating the velocity of reciprocating elements of injection pump assembly 40 in a closed-loop manner. For example, referring to FIG. 2, where sufficient precision can be obtained by regulating output flow from pump 50 via positioner 54, valving 46 may include conventional directional control valving, rather than a servo valve. In this alternative embodiment, flow from injection pump driver 38 is regulated by control of positioner 54 via control signals supplied by controller 36, as indicated by the broken line between these elements in FIG. 2. Unlike conventional injection pump drive systems, however, the velocity of reciprocating components of injection pump assembly 40 is again controlled in a closed-loop manner by regulating flow rate of pump 50 based upon feedback signals from sensor assembly 92 as described above. Similarly, depending upon the precision desired, pump controller 36 may include circuitry designed to regulate the rotational speed of motor 48. As will be appreciated by those skilled in the art, such circuitry may include a voltage-source, variable-frequency inverter drive. In such arrangements, motor 48 could be driven at desired speeds to produce flow rates from pump 50 at levels needed to ensure the commanded velocity of reciprocating components of injection pump assembly 40 as described above.

Figure 5:
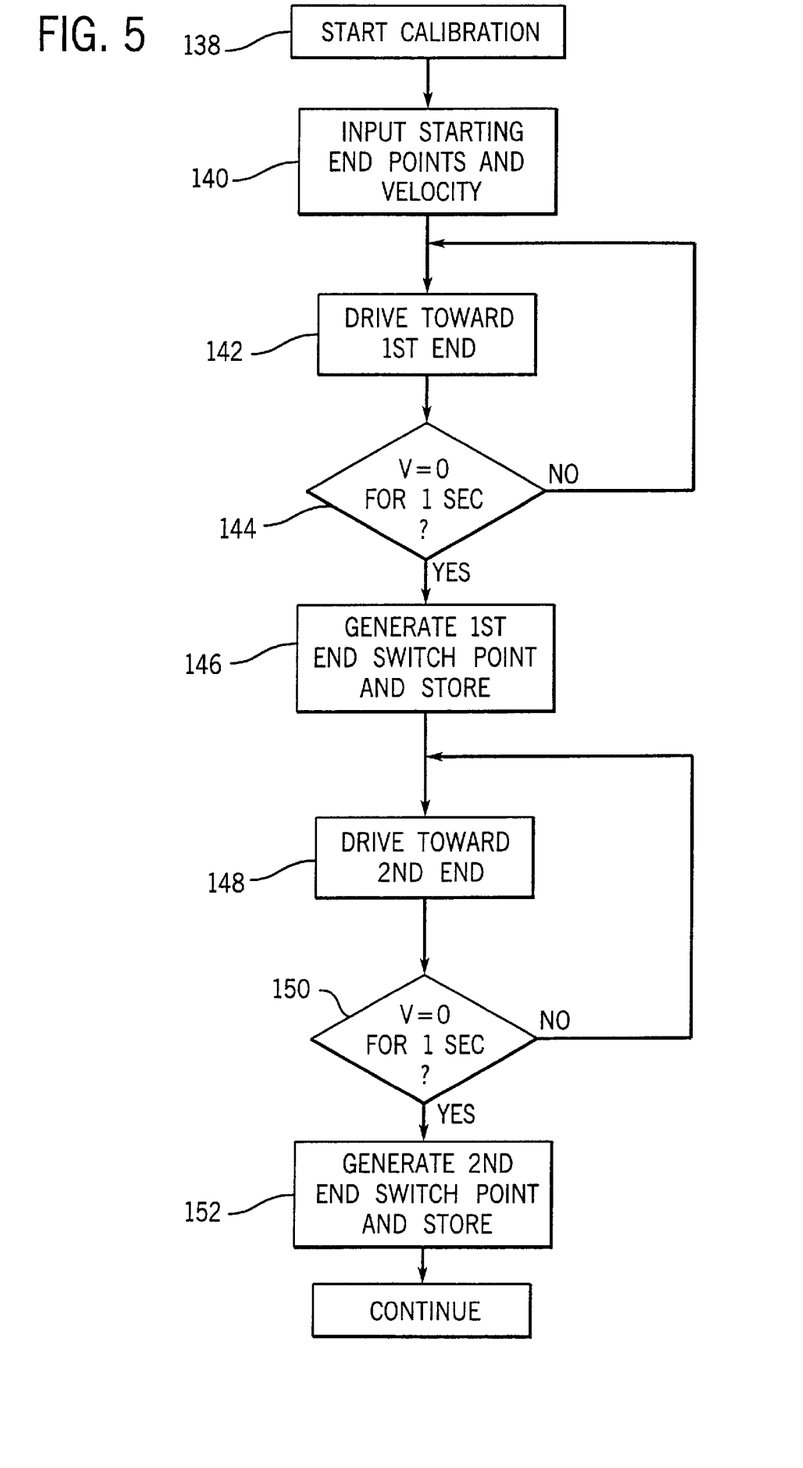
FIG. 5 is a flow chart illustrating steps of exemplary control logic used to calibrate an injection system of the type illustrated in FIG. 2.

FIG. 5 illustrates certain steps of exemplary control logic used to calibrate injection system 10. In the presently preferred embodiment, injection pump assembly 40 is driven continuously in reciprocation between predetermined stroke limits stored in memory circuit 134. The calibration procedure illustrated in FIG. 5 permits operation personnel or an automatic process controller to assign desired stroke limits or end switch points during initiation of system 10 or subsequent calibration.

As illustrated in FIG. 5, the calibration procedure begins at step 138. At step 140, default end points and calibration velocity values are accessed from a memory circuit within controller 36. Alternatively, the operator may be prompted to input starting end points and a calibration velocity via human interface and display station 94. In a presently preferred configuration, for example, a calibration velocity may be set at anywhere within a velocity range of zero to 1.5 inches per second. Moreover, while end points may set at any location between the physical limits of drive cylinder 66 (i.e., locations where piston 70 contacts heads 98, or where plungers 76 contact ends of bores 112), for calibration purposes, controller 36 may be permitted to locate the physical stroke limits as follows.

At step 142, controller 36 shifts valving 46 to drive piston 70 towards a first end of drive cylinder 66 at the velocity of input at step 140. At step 144, central processing circuit 130 polls velocity feedback signals received from conversion circuit 42 to determine whether the reciprocating components of assembly 40 have remained stationary (i.e., at a zero velocity) for one second. If not, control returns to step 142 and piston 70 continues to be driven towards the first end. When central processing circuit 130 detects that the reciprocating components of assembly 40 have stopped for one second, a first physical end switch point is derived from the position indicated by sensor assembly 92 and is stored in memory as indicated at step 146. In a presently preferred embodiment, the position indicated by assembly 92 is offset by ⅛ inch to determine the end switch point to avoid physically contacting elements of assembly 40 during normal operation.

Central processing circuit 130 then proceeds to step 148 to drive piston 70 towards the opposite end of drive cylinder 66 at the velocity input at step 140. At step 150, central processing circuit 130 polls the velocity feedback signal from conversion circuit 42 to determine whether the piston has again reached zero velocity and maintained this level for one second. If the piston has not stopped, control returns to step 148 and valve 46 remains in a position to drive the piston toward the second end. Once the velocity feedback signal is determined to have remained at a level of zero for one second, central processing circuit 130 proceeds to step 152 to read the position signal generated by sensor assembly 92 and to derive the second end switch point or stroke limit from the position signal. Once again, the second end switch point is preferably offset from the physical limit by ⅛ inch. Once the two physical stroke limits have been located and stored, central processing circuit 130 exits the calibration routine.

Although the routine described above permits controller 36 automatically to determine physical stroke limits of the injection pump assembly, in the preferred embodiment the stroke limits used during steady state operation of injection system 10 can be subsequently altered between these physical stroke limits by intervention of an operator via human interface and display station 94, or by a process controller. It should also be noted that the calibration sequence described above permits the foregoing system automatically to compensate for the particular physical configuration (i.e., size, length, tolerance variations) of the injection pump assembly to which the drive system is applied. Thus, the drive and control system described above may be easily retrofit to existing reciprocating pump assemblies and calibrated by the foregoing procedure without the need to preconfigure the system with information specific to the pump assemblies.

While the invention may be susceptible to various modifications and alternative forms, specific embodiments have been shown in the drawings and have been described in detail herein by way of example only. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An injection pump system comprising:
    a pump body including a metering section and a drive section coaxially coupled to the metering section;
    a reciprocating assembly, the reciprocating assembly including a plunger disposed in the metering section, a piston disposed in the drive section, and a rod drivingly coupled to the piston and the plunger;
    a drive pump unit coupled to the drive section for supplying pressurized fluid for forcing reciprocation of the reciprocating assembly with respect to the pump body between predetermined stroke limits;
    a sensor assembly configured to generate a parameter signal representative of position of the reciprocating assembly with respect to the pump body bidirectionally during reciprocation of the reciprocating assembly between the stroke limits; and
    a control circuit coupled to the drive pump unit and to the sensor assembly, the control circuit being configured to generate a velocity signal from the parameter signal, to compare the velocity signal to a velocity command signal, and to regulate flow of pressurized fluid from the drive pump unit to the drive section and thereby to regulate reciprocating motion and bidirectional reversing of the reciprocating assembly based upon the velocity signal and the velocity command signal.

2. The injection pump system of claim 1, wherein the sensor assembly includes a position sensor set coupled to the pump body and the reciprocating assembly, the position sensor set being configured to generate a signal representative of the position of the reciprocating assembly with respect to the pump body during movement of the reciprocating assembly between the stroke limits.

3. The injection pump system of claim 1, wherein pump system is configured to inject a pressurized catalyst into a process stream, and wherein the velocity command signal is derived from an operating parameter of the process stream.

4. The injection pump system of claim 1, wherein the pump body includes a first metering section disposed on a first side of the drive section and a second metering section disposed on a second side of the drive section, and wherein the reciprocating assembly includes a first plunger disposed in the first metering section and a second plunger disposed in the second metering section, each plunger being drivingly coupled to a rod extending from the piston.

5. The injection pump system of claim 1, wherein the drive pump unit includes an electrohydraulic metering valve assembly, and wherein the control circuit is configured to generate a flow control signal based upon the velocity signal and the velocity command signal and to apply the flow control signal to the metering valve assembly to regulate the flow of pressurized fluid from the drive pump unit to the drive section.

6. The injection pump system of claim 1, wherein the control circuit is configured to compare the parameter signal to stroke limit values of the reciprocating assembly, and automatically to command reversal of a direction of travel of the reciprocating assembly based upon the parameter signal and the stroke limit values.

7. An injection pump drive system for controlling a reciprocating injection pump, the injection pump comprising a pump body including a metering section and a drive section coaxially coupled to the metering section, and a reciprocating assembly including a plunger disposed in the metering section, a piston disposed in the drive section, and a rod drivingly coupled to the piston and the plunger, the reciprocating assembly being movable with respect to the pump body in first and second directions between predetermined stroke limits, the drive system comprising:
    a drive pump unit coupled to the drive section;
    a sensor assembly configured to generate an input signal indicative of actual velocity of the reciprocating assembly during movement of the reciprocating assembly in the first and second directions between the stroke limits; and
    a control circuit coupled to the sensor assembly and to the drive pump unit, the control circuit being configured to compare the input signal to a command signal indicative of a desired flow rate from the injection pump, to generate control signals based upon the input and command signals, and to apply the control signals to the drive pump unit to regulate flow of pressurized fluid from the drive pump unit, and thereby to control the flow rate from the injection pump.

8. The injection pump system of claim 7, wherein the sensor assembly includes a position sensor assembly coupled to the reciprocating assembly for generating position signals during movement of the reciprocating assembly between the stroke limits.

9. The injection pump system of claim 8, wherein the input signals are representative of actual velocity of the reciprocating assembly with respect to the pump body and the command signals are representative of desired velocity of the reciprocating assembly with respect to the pump body.

10. The injection pump system of claim 9, wherein the control circuit is configured to derive the actual velocity signals from the position signals.

11. The injection pump system of claim 7, wherein the drive pump unit includes a metering valve assembly, and wherein the control circuit is configured to generate a flow control signal based upon the input signal and the command signal and to apply the flow control signal to the metering valve assembly to regulate the flow of pressurized fluid to the drive section.

12. The injection pump system of claim 7, wherein the drive pump includes a controllable variable volume drive pump assembly, and wherein the control circuit is configured to generate a flow control signal based upon the input signal and the command signal and to apply the flow control signal to the drive pump assembly to regulate the flow of pressurized fluid to the drive section.

13. A method for metering pressurized flow from a reciprocating injection pump, the injection pump including a pump body having a metering section and a drive section coaxially coupled to the metering section, a reciprocating assembly comprising a plunger disposed in the metering section, a piston disposed in the drive section, and a rod drivingly coupled to the piston and the plunger, and a drive pump unit coupled to the drive section for supplying a flow of pressurized fluid for forcing reciprocation of the reciprocating assembly in first and second directions with respect to the pump body between predetermined stroke limits at desired velocities, the method comprising the steps of:

(a) generating a velocity command signal representative of a desired velocity of the reciprocating assembly with respect to the pump body;

(b) generating an actual velocity signal representative of the actual velocity the reciprocating assembly in the first and second directions with respect to the pump body;

(c) comparing the velocity command signal and the actual velocity signal, and generating a drive command signal based thereon for velocity control of the reciprocating assembly in the first and second directions; and (d) regulating the flow of pressurized fluid from the drive pump unit to the drive section based upon the drive command signal.

14. The method of claim 13, comprising the steps of sensing position of the reciprocating assembly with respect to the pump body between the predetermined stroke limits to generate position signals, and generating the actual velocity signal based upon the position signals.

15. The method of claim 13, wherein the injection pump is configured to inject catalyst into a process stream, and wherein the velocity command signal is derived from an operating parameter of the process stream.

16. The method of claim 13, wherein the drive pump unit includes a metering valve assembly for metering flow of pressurized fluid from a drive pump to the drive section, and wherein at step (d) the drive command signal is applied to the metering valve assembly to regulate the flow of pressurized fluid from the drive pump unit to the drive section.

17. The method of claim 13, wherein the drive pump unit includes a controllable variable volume drive pump assembly, and wherein at step (d) the drive command signal to the drive pump assembly to regulate the flow of pressurized fluid to the drive section.

18. A method for controlling rate of chemical injection into a process stream by a reciprocating injection pump, the injection pump including a pump body having a metering section and a drive section coaxially coupled to the metering section, a reciprocating assembly comprising a plunger disposed in the metering section, a piston disposed in the drive section, and a rod drivingly coupled to the piston and the plunger, and a drive pump unit coupled to the drive section for supplying a flow of pressurized fluid for forcing reciprocation of the reciprocating assembly with respect to the pump body between predetermined stroke limits at desired velocities, the method comprising the steps of:

(a) sensing a parameter of the process stream and generating a parameter signal representative thereof;

(b) deriving an injection rate command signal from the parameter signal;

(c) converting the injection rate command signal to an injection pump velocity command signal;

(d) driving the reciprocating assembly at a predetermined velocity with respect to the pump body based upon the velocity command signal;

(e) generating an actual velocity signal representative of the velocity of the reciprocating assembly with respect to the pump body;

(f) comparing the actual velocity signal to the velocity command signal; and (g) regulating the velocity of the reciprocating assembly to maintain the velocity of the reciprocating assembly at a desired level.

19. The method of claim 18, wherein step (e) comprises the steps of sensing positions of the reciprocating assembly between the stroke limits and generating position signals representative thereof, and wherein the actual velocity signal is derived from the position signals.

20. The method of claim 18, wherein the drive pump unit includes a metering valve assembly for metering flow of pressurized fluid from a drive pump to the drive section, and wherein at step (g) flow from the metering valve assembly is controlled to regulate the velocity of the reciprocating assembly.

21. The method of claim 18, wherein the drive pump unit includes a controllable variable volume drive pump assembly, and wherein at step (g) flow of pressurized fluid from the drive pump assembly to the drive section is controlled to regulate the velocity of the reciprocating assembly.

* * * * *